(12) United States Patent
Ra et al.

(10) Patent No.: US 8,470,378 B2
(45) Date of Patent: Jun. 25, 2013

(54) **ANTI-INFLUENZA VIRAL COMPOSITION CONTAINING BARK OR STEM EXTRACT OF *ALNUS JAPONICA***

(75) Inventors: Jeong Chan Ra, Gyeonggi-do (KR); Hyuk Joon Kwon, Seoul (KR); Byeung Gie Kim, Gyeonggi-do (KR); Seok Hyon You, Seoul (KR)

(73) Assignee: RNL Bio Co., Ltd, Seoul (KR)

( * ) Notice: Subject to any disclaimer, the term of this patent is extended or adjusted under 35 U.S.C. 154(b) by 0 days.

(21) Appl. No.: 13/414,197

(22) Filed: Mar. 7, 2012

(65) Prior Publication Data

US 2012/0164253 A1 Jun. 28, 2012

Related U.S. Application Data

(62) Division of application No. 12/747,289, filed as application No. PCT/KR2008/007172 on Dec. 4, 2008, now abandoned.

(30) Foreign Application Priority Data

Dec. 11, 2007 (KR) .................. 10-2007-0127996

(51) Int. Cl.
*A61K 36/00* (2006.01)
(52) U.S. Cl.
USPC ........................................................ 424/725
(58) Field of Classification Search
None
See application file for complete search history.

(56) References Cited

U.S. PATENT DOCUMENTS

| | | | |
|---|---|---|---|
| 6,544,530 B1 | 4/2003 | Friedman | |
| 6,680,076 B2 | 1/2004 | Nam | |
| 2005/0222269 A1* | 10/2005 | Tatton et al. | 514/649 |
| 2007/0032558 A1* | 2/2007 | Lerner et al. | 514/743 |

FOREIGN PATENT DOCUMENTS

| | | |
|---|---|---|
| JP | 08239307 A | 9/1996 |
| KR | 20030074500 A | 9/2003 |
| KR | 10-2004-0016578 A | 2/2004 |
| KR | 1020060023093 A | 3/2006 |
| KR | 620511 B1 | 9/2006 |
| KR | 100708593 B1 | 4/2007 |
| KR | 1020060026591 A | 4/2007 |
| KR | 100721703 B1 | 5/2007 |
| KR | 100769050 B1 | 10/2007 |
| WO | 00/40269 A2 | 7/2000 |
| WO | 2008/001976 A1 | 1/2008 |

OTHER PUBLICATIONS

Balch, Prescription for Nutritional Healing, fourth edition, section element of health, p. 98, copyrighted 2006.
Yu Young-Beob et al., Effects of triterpenoids and flavonoids isolated from *Alnus* firma on HIV-1 viral enzymes, Archives of Pharmacal Research, 2007, vol. 30, pp. 820-826.
Supplementary European Search Report and Opinion for EP 08 85 8731, issued Jun. 5, 2011 by the European Patent Office.

* cited by examiner

*Primary Examiner* — Michele Flood
*Assistant Examiner* — Randall Winston
(74) *Attorney, Agent, or Firm* — Tristan A. Fuierer; Andrew D. Gerschutz; Moore & Van Allen, PLLC

(57) ABSTRACT

The present invention relates to an antiviral composition comprising an *Alnus japonica* extract, more specifically, relates to a method for preparing high activated anti-influenza viral composition, which comprises an extract of the bark or stem of *Alnus japonica*, and an anti-influenza viral composition comprising the extract. An extract of the bark or stem of *Alnus japonica* according to the present invention has low toxicity to normal cells, while having an excellent antiviral effect even when administered at low concentration and thus the composition comprising the *Alnus japonica* extract can be used effectively in preventing and treating influenza viral infection.

6 Claims, No Drawings

ANTI-INFLUENZA VIRAL COMPOSITION CONTAINING BARK OR STEM EXTRACT OF *ALNUS JAPONICA*

CROSS-REFERENCE TO RELATED APPLICATIONS

This application is a divisional application of and claims the priority of U.S. patent application Ser. No. 12/747,289 filed on Jun. 10, 2010 entitled "Anti-Influenza Viral Composition Containing Bark or Stem Extract of Alnus Japonica" in the name of Jeong Chan RA, et al., which claims priority of International Patent Application NO. PCT/KR2008/007172 filed on Dec. 4, 2008, which claims priority of Korean patent application Ser. No. 10/2007-0127996, filed Dec. 11, 2007, all of which are hereby incorporated by reference herein in their entireties.

TECHNICAL FIELD

The present invention relates to an antiviral composition comprising an *Alnus japonica* extract, more specifically, relates to a method for preparing an extract of the bark or stem of *Alnus japonica*, which has high anti-influenza viral activity, and an anti-influenza viral composition comprising the extract.

BACKGROUND ART

Avian influenza virus belongs to the orthomixoviridae family, and causes damage to poultry such as chicken, turkey. Avian influenza viruses are classified into 3 types of high-pathogenic, low-pathogenic and non-pathogenic avian influenza viruses according to the degree of pathogenicity, among which the high-pathogenic virus is classified as an OIE List A disease by the World Organization for Animal Health (OIE) and "a category 1 domestic animal infectious disease" in Republic of Korea.

Influenza virus is classified as type A, B or C according to the antigenicity of nucleocapsid protein and matrix protein. Moreover, according to the difference of antigen structure of haemagglutinin (HA) and neuraminidase (NA), the HA is classified into 16 subtypes and NA is classified into 9 subtypes, wherein HA helps host cell receptor binding, and fusion between host cell membrane and viral envelope to cause virus infection and NA plays an important role when virus buds out through the cell membrane after proliferation. Theoretically, 144 kinds of virus subtypes could exist by the combination of two proteins.

Infection generally occurs by contact with contaminated secretions, furthermore, and it could be spread through the air, in both particle and droplet forms, human feet, feed delivery vehicles, apparatuses and feces on the surface of eggs etc. Although there are various symptoms according to the pathogenicity of infecting virus, generally, they are respiratory symptoms, diarrhea and a sharp decline in egg production etc. Moreover, in some cases, cyanosis appears in the head region such as crest, edema appears on the face, or feathers are ruffled. Mortality rate also varies from 0% to 100% according to pathogenicity, but since the symptoms are similar to those of Newcastle Disease, infectious larynogotracheitis, mycoplasma infection and the like, an accurate diagnosis is required.

High pathogenic avian influenza had occurred 23 times from 1959 to 2003 throughout the world, most of them were endemic and contained. The outbreaks of highly pathogenic avian influenza subtype H5N1 had occurred in Korea in December 2003, occurred in more than 30 countries including Europe, Africa and most countries in Southeast Asia such as Japan, China, Thailand, Vietnam and Indonesia and thus have become pandemic. Although it is known that humans cannot become infected with avian influenza, prevention of avian influenza is of paramount importance to public health sector since the case of human infection with H5N1 in 1997, isolation of H9N2 avian influenza viruses from humans in 1999 in Hong Kong and human cases of H7 avian influenza infection in 2004 in Canada. According to a report of the World Health Organization (WHO), (http://www.who.int/csr/disease/avian_influenza/country/cases_table_2006_06_20/e n/index.html), it was confirmed that 228 persons had been infected with H5N1 subtype viruses and 130 persons of them died during the period of 2003 to Jun. 20, 2006 in 10 countries. In Korea, since an outbreak of low pathogenic avian influenza by H9N2 subtype viruses had occurred in 1996 and it reoccurred in 1999.

If an avian influenza outbreak occurs, in most countries, the poultry needs to be disposed of, and countries where avian influenza outbreaks have occurred cannot export poultry products, thus causing swingeing damages to poultry industry.

Furthermore, when there is a risk of human infection, the damages spread to the whole industry including the tourism industry and the transport industry, thus causing astronomical loss.

Natural substance refers to substances which are minimally processed without artificial ingredients, and the natural substances classified as GRAS (Generally Recognized As Safe) can be used without restrictions on the quantity thereof or foods in which the natural substances are to be used. In domestic industry, the natural substances are classified as natural additives, and used as food additives, and in foreign countries, it has been used as health foods and medical supplies for user's purpose without extra limitation, because of its excellent functionality.

Meanwhile, *Alnus japonica* is a deciduous, dicotyledonous tree in the order Fagales, family Betulaceae, which is commonly called *Alnus japonica* tree. They are distributed in Korea, Japan, China, etc., and grow in marsh conditions, its height is about 20 m and its bark is a deep purplish-brown color. Its winter bud is a long oval shape just like the shape of an egg turned upside down, which has three lines and a peduncle. The leaves of *Alnus japonica* grow alternately, and they are oval shaped, egg-shaped (more or less round on both ends, widest at the bottom) or lanceolate. Both sides of a leaf are lustrous and leaf margins are saw-toothed. The flowers of *Alnus japonica* bloom in March~April, are unisexual, and form a catkin. Staminate spike bears staminate flower and each bract subtends 3~4 flowers. There are four perianths and four stamens in each flower. Fruit ripens in October and 2~6 fruits are produced. It is long egg-shaped and looks like a pine cone.

Examples of conventional patents relating to *Alnus japonica* extracts include a cosmetic composition containing an *Alnus japonica* extract (Korean Patent Publication No. 10-2003-0074500) and a method for preparing a health drink useful for relieving hangovers, which comprises extracts of *Alnus japonica* and green tea leaves (Korean Patent Publication No. 10-2006-0023093), etc.

Recently, many research endeavors are taking place to develop anti-viral agents throughout the world. Lamibudine used for the treatment of HIV (Human Immunodeficiency Virus)-1 and hepatitis B, gancyclovir used for the treatment of symptoms of herpes virus infection, ribavirin which is used mainly for the treatment of symptoms of respiratory syncytial virus infection but can be used for the treatment of symptoms of various virus infection when it is an emergency and zanamivir RELENZA™ and oseltamivir TAMIFLU™ which are synthesized artificially as influenza virus neuraminidase inhibitors are all commercially available after gaining approval. However, use of amantadine and its analogue, rimantadine, which are approved for treatment of influenza virus A, has decreased due to the appearance of resistant virus and its side effect. Recently, virus resistant to oseltamivir among H5N1 avian influenza viruses appeared, therefore, there is an urgent need to develop various antiviral agents.

The present inventors have confirmed antiviral activity of methanol extract of *Alnus japonica* in Korean Patent Registration No. 10-0721703 and Korean Patent Registration No. 10-0769050. However, the above mentioned patents have a disadvantage of showing antiviral activity only when the extracts were administered at high concentration and thus the possible applications thereof are limited.

Therefore, the present inventors have made an extensive effort to develop a natural substance having a low toxicity to normal cells, while having an excellent effect of inhibiting influenza virus proliferation even when administered at low concentration, and as a result, confirmed that an extract obtained by extracting the bark or stem of *Alnus japonica*, which is indigenous to Korea, with 8~90% ethanol at 30~80° C., has an excellent anti-influenza virus effect, thereby completing the present invention.

SUMMARY OF INVENTION

It is a main object of the present invention to provide a method for preparing an extract of the bark or stem of *Alnus japonica*, which has high anti-influenza viral activity.

It is another object of the present invention to provide a food composition for preventing or improving influenza viral infection, which comprises an extract of the bark or stem of *Alnus japonica*, prepared by the above method.

It is still another object of the present invention to provide a pharmaceutical composition for preventing or treating influenza viral infection, which comprises an extract of the bark or stem of *Alnus japonica*, prepared by the above method.

In order to achieve the above objects, the present invention provides a method for preparing an extract of the bark or stem of *Alnus japonica*, which has anti-influenza viral activity, the method comprising the steps of: (a) extracting the bark or stem of Korean indigenous *Alnus japonica* with 80~100% ethanol at 30~80° C.; and (b) recovering the resulting extraction solution.

The present invention also provides a food composition for preventing or improving influenza viral infection, which comprises an extract of the bark or stem of *Alnus japonica*, prepared by the above method, and a sitologically acceptable supplemental additive.

The present invention also provides a pharmaceutical composition for preventing or treating influenza viral infection, which comprises an extract of the bark or stem of *Alnus japonica*, prepared by the above method, as an active ingredient.

The present invention also provides use of an extract of the bark or stem of *Alnus japonica* prepared by the above method for preventing or treating influenza viral infection.

The present invention also provides a method for preventing or treating influenza viral infection using an extract of the bark or stem of *Alnus japonica* prepared by the above method.

In the present invention, the influenza virus is preferably selected from the group consisting of: human influenza virus, swine influenza virus, equine influenza virus and avian influenza virus. Preferably, the avian influenza virus is KBNP-0028 (KCTC 10866BP).

Other features and examples of the present invention will be further clarified from the following detailed description and the appended claims.

DETAILED DESCRIPTION OF THE INVENTION, AND PREFERRED EMBODIMENTS

In one aspect, the present invention relates to a method for preparing an extract of the bark or stem of *Alnus japonica*, which has anti-influenza viral activity, the method comprising the steps of: (a) extracting the bark or stem of Korean indigenous *Alnus japonica* with 80~100% ethanol at 30~80° C.; and (b) recovering the resulting extraction solution.

In one embodiment of the present invention, after the bark or stem of *Alnus japonica* was powdered and extracted with water or ethanol by hot water extraction, cold water extraction, reflux-cooling extraction or ultrasonic extraction, then centrifuged, thus obtaining an extract of the bark or stem of *Alnus japonica*.

In the present invention, after a composition containing an extract of the bark or stem of *Alnus japonica* was added to SPF embryonated eggs infected with avian influenza virus and cultured, the plate hemagglutination test was performed, and as a result, it was confirmed that the composition containing an extract of the bark or stem of *Alnus japonica* has excellent anti-influenza viral effect even when administered at low concentration.

In another aspect, the present invention relates to a pharmaceutical composition for preventing or treating influenza viral infection (influenza viral disease), which comprises an extract of the bark or stem of *Alnus japonica*, prepared by the above method, as an active ingredient.

In the present invention, influenza virus is preferably selected from the group consisting of: human influenza virus, swine influenza virus, equine influenza virus, and avian influenza virus. More preferably, avian influenza virus is KBNP-0028 (KCTC 10866BP).

The inventive extract of the bark or stem of *Alnus japonica* is a natural substance and thus has no toxicity, which enables long-term administration in high dosage as a medical product.

A composition comprising the inventive extract of the bark or stem of *Alnus japonica* can be prepared by mixing together with pharmaceutical agents such as antihistaminic agents, anti-inflammatory analgesic agents, anti-cancer agents and antibiotics, or can be used in combination therewith.

The composition of the present invention in pharmaceutical dosage forms may be used in the form of pharmaceutically acceptable salts, and also may be used alone or in appropriate association, as well as in combination with other pharmaceutically active compounds.

The pharmaceutical composition comprising the inventive extract may be formulated into an oral preparation such as powders, granules, tablets, capsules, suspensions, emulsions, syrups, aerosols etc, an external preparation, a suppository and a sterile injectable solution, according to the conventional preparation methods. The pharmaceutical composition comprising the inventive extract may comprise carriers, excipients and diluents, and examples of suitable carriers, excipients and diluents include lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinyl pyrrolidone, water, methylhydroxy benzoate, propylhydroxy benzoate, talc, magnesium stearate and mineral oil.

The composition of the present invention can be formulated into a preparation form, together with the conventional diluents or excipients such as fillers, extenders, binders, wetting agents, disintegrants, surfactants etc. A solid preparation for oral administration includes tablets, pills, powders, granules, capsules etc, and the solid preparation is formulated by mixing the extract with at least one excipient, for example, starch, calcium carbonate, sucrose, lactose, gelatin and the like. Also, a lubricant such as magnesium stearate and talc is used in addition to the excipients. A liquid preparation for oral administration includes suspension, zipeprol, emulsion, syrup and the like, and various excipients, for example, wetting agents, flavoring agents, fragrances, preservatives etc, can be contained thereto in addition to conventional diluents such as water and liquid paraffin A preparation for parenteral administration includes sterile aqueous solution, non-aqueous solution, suspensions, emulsions, a lyophilized preparation, and suppositories. Examples of non-aqueous solution and suspensions include vegetable oil such as propylene glycol, polyethylene glycol and olive oil, and injectable esters such as ethyloleate and the like. Base materials of suppositories include witepsol, macrogol, tween 60, cacao butter, laurin butter, glycerol gelatine and the like.

Although the dosage of the extract according to the present invention varies depending on the weight and condition of a patient, the severity of the disease, the dosage form, administration route, and treatment period, the dosage can be properly determined by a person skilled in the art. However, in order to achieve the desired effect, the inventive extract is administered at a dose of 0.01-200 mg/kg per day, preferably 0.1-100 mg/kg per day. The foregoing doses may be administered as a single dose or may be divided into multiple doses per day, and the doses do not limit the scope of the present invention in any way.

The inventive extract can be administered to mammals including rats, mice, domestic animals, humans and the like via various routes. The mode of administration may include, for example, oral and rectal administration, or venous, muscular, subcutaneous, endometrium or intracerebroventricular injections.

In another aspect, the present invention provides a food composition for preventing or improving influenza viral infection, which comprises an extract of the bark or stem of *Alnus japonica*, prepared by the above method, and a sitologically acceptable supplemental additive.

In an embodiment of this aspect, the influenza virus is preferably selected from the group consisting of: human influenza virus, swine influenza virus, equine influenza virus and avian influenza virus. More preferably, the avian influenza virus is KBNP-0028 (KCTC 10866BP).

The composition comprising the inventive extract or pharmaceutically acceptable salts thereof can be used as a main ingredient, food additive and supplement when preparing various functional foods and health functional foods.

In the present invention, the term "functional foods" refers to a food whose functionality is improved by adding the inventive extract thereto. Functionality can be broadly divided into physical functionality such as synthetic flavors and natural flavors physiological functionality. When the inventive extract is added to a general food, such as synthetic flavors and natural flavors and physiological functionality thereof will be improved. Therefore, in the present invention, the food with improved functionality is broadly defined as functional foods.

Aside from the above, the inventive extract may contain various nutrients, vitamins, minerals (electrolytes), flavors such as synthetic flavors and natural flavors, coloring matters, enhancer (cheese, chocolate, etc.) pectic acid and its salts, alginic acid and its salts, organic acids, protective colloid thickners, pH control agents, stabilizers, preservatives, glycerins, alcohols and carbonating agents for carbonated beverage use, etc. In addition, the extract of the present invention may contain natural fruit juices, and fruit pulps for the provision of fruit juice drinks and vegetable drinks These ingredients can be used independently or in combination. The proportion of these additives is not so critical, but generally selected from the range of 0.01~20 parts by weight based on 100 parts by weight of the inventive extract.

EXAMPLES

Hereinafter, the present invention will be described in more detail by examples. However, it is obvious to a person skilled in the art that these examples are for illustrative purpose only and are not construed to limit the scope of the present invention.

Example 1

Preparation of *Alnus japonica* Extract 1-1: Preparation of Extraction Solvent and Extraction at Various Temperatures The bark of Korean indigenous *Alnus japonica* purchased from Kyungdong market, Seoul, Korea was dried at room temperature for 24 hrs, finely chopped and pulverized. 1 kg of the obtained bark fragments were extracted with 10L of 95% ethanol under reflux for 8 hrs at 40° C., 60° C. and 80° C. or extracted with 10L water under reflux for 4 hrs at 100° C., and filtered under vacuum to collect supernatant, followed by eluting useful substances from the obtained fragments. The eluted useful substances are dried under vacuum for 24 hrs to obtain 100 g of *Alnus japonica* powder, and the obtained powder was dissolved in 99.9% dimethyl sulfoxide (DMSO) solution to a concentration of 20 mg/ml, then used for the following experiments.

For comparison experiments, *Alnus japonica* bark extracts prepared by the method in example 1 of Korean Patent Registration No. 10-0721703 and Korean Patent Registration No. 10-0769050 (an antiviral composition comprising *Alnus japonica* extracts), as a control group.

1-2: Preparation of *Alnus japonica* Extracts using *Alnus japonica* from Different Origins The bark and stem of Korean indigenous *Alnus japonica* purchased from Kyungdong market, Seoul, Korea and the bark of Chinese native *Alnus japonica* purchased from Yanbian market in China were dried at room temperature for 24 hrs, finely chopped and pulverized. 1 kg of the obtained *Alnus japonica* fragments were extracted with 10L of 80% ethanol and 95% ethanol under reflux at 40° C., respectively, and filtered under vacuum to collect supernatant, followed by eluting useful substances from the obtained fragments. The eluted useful substances are dried under vacuum for 24 hrs to obtain 100 g of *Alnus japonica* powder was obtained, and the obtained powder was dissolved in 99.9% dimethyl sulfoxide (DMSO) solution to a concentration of 20 mg/ml, then used for the following experiments.

Example 2

Examination of Anti-Viral Effect of *Alnus japonica* Extracts

2-1: Preparation of KBNP-0028

As avian influenza virus used in the experiment, hyperproliferative KBNP-0028 (KR 2006-0026591) cloned after subculturing A/chicken/Korea/SNU0028/2000(H9N2) virus (it is isolated in Korea in 2000) in chick embryo was used. That is, SNU0028 [A/chicken/Korea/SNU0028/2000(H9N2); isolation and report to National Veterinary Research and Quarantine Service, May 9, 2005] is low-pathogenic avian influenza virus of H9N2 subtype, and isolated from chickens showing mortality and egg drop syndrome in a chicken farm located in North jeola Province in Jan. 28, 2000. The isolation method is as follows: after kidney and tracheal samples from infected chickens are dissolved, suspended in phosphate buffer, and filterated with 0.45 μm filter paper, each sample is inoculated into three allantoic cavities of SPF (Specific Pathogen Free) embryonated egg (Sunrise Co., NY), and cultured at 37° C. to obtain allantoic fluid. 20 μl of the allantoic fluid and 20 μl of 0.1% chicken red blood cells, extracted from a chicken hatched from the SPF embryonated egg, are dropped on a glass plate, and mixed to carry out the plate hemagglutination test.

As a result, in all of the allantoic fluids, obtained by inoculating the kidney sample and tracheal sample, hemagglutination occurred. The virus was identified with RT-PCR using H9N2 specific primer and base sequence analysis (Kim Min Chul, Master's Thesis, 2002, Seoul National University), and stored at −70° C. Among them, the virus isolated from tracheal sample was used in the experiment.

In order to select a vaccinia strain having high productivity in embryonated eggs, the SNU0028 was diluted with a phosphate buffer solution to a concentration of 0.05 to 0.5 HAU/ml, and 200 μl of the diluted solution was inoculated into the allantoic cavity of 10-11-day-old SPF embryonated eggs (Sunrise Co., NY), then cultured for three days at 37° C. Every day, the embryonated eggs, which died three days ago, were discarded through egg examination in the morning and afternoon. The embryonated eggs, which survived for three days, were stored for 12~24 hrs at 4° C., from which allantoic fluid was harvested to measure the volume and hemagglutination titer of each egg. Among them, allantoic fluid having the most quantity and the highest hemagglutination titer was inoculated into embryonated eggs using the same method as described above, and subcultured 19 times to select allantoic fluid whose productivity was increased showing high hemagglutination titer and high yield thereof, and thus, the strain was named KBNP-0028 and deposited in GenBank located Eoeundong, Youseonggu, Daejeon city, Korea on Oct. 26, 2005 (KCTC 10866BP).

2-2: Culturing Embryonated Egg Shell Fragments

The egg shell of 10~11-day-old SPF embryonated eggs (Sunrise Co., NY) was washed with 70% ethanol and chick embryo and all body fluids were removed. The resulting egg shell was cut into pieces about 8 mm long and 8 mm wide while maintaining villi and allantois adhered to the inner surface of the egg shell, and each piece was added into a 24-well culture plate. Culture medium was prepared by (i) mixing 199 medium (GIBCO-BRL, NY, USA) with F10 medium (GIBCO-BRL, NY, USA) at a ratio of 1:1, (ii) adding 0.075% of sodium bicarbonate and 100 μg/ml of gentamicin.

The 10~11-day-old SPF embryonated eggs (Sunrise Co., NY) were infected with virus by adding 100 μl of the crude allantoic fluids, KBNP-0028 prepared in Example 2-1, which is 4~10-fold diluted, to the villi and allantois of embryonated egg shell fragments, and culturing for 30 min at 37° C., and added with 1000 μl of the culture medium, then *Alnus japonica* extracts prepared in Example 1-1 and Example 1-2 was added to 6 well plates at various concentration, respectively, followed by culturing for 7 days at 37° C.

2-3: Test of Antiviral Effect

Culture broth of said virus-infected fluids cultured for 7 days in Example 2-2, which is added with *Alnus japonica* extracts at various concentrations, was taken to carry out plate hemagglutination test. 25 μl of the culture broth and 25 μl of chicken red blood cells (0.1%) were dropped on a glass plate and mixed evenly. Virus proliferation was determined according to whether hemagglutination occurred within 2 min by moving the glass plate right and left, and up and down.

TABLE 1

| Control | | | *Alnus japonica* extracts (μg/ml) | | | |
|---|---|---|---|---|---|---|
| virus | non-virus | Extract solvent | 400 | 200 | 100 | 50 |
| 6/6 | 0/6 | 80° C., 95% ethanol | 0/6 | 0/6 | 2/6 | 5/6 |
| | | 60° C., 95% ethanol | 0/6 | 0/6 | 2/6 | 5/6 |
| | | 40° C., 95% ethanol | 0/6 | 0/6 | 1/6 | 3/6 |
| | | 100° C., water | 1/6 | 4/6 | 6/6 | 6/6 |
| | | 99.9% methanol | 0/6 | 2/6 | 6/6 | — |

As a result, as shown in Table 1, in the sample added with 100° C. water extract as a negative control, hemagglutination occurred in one of 6 test samples at 400 μg/ml, showing partial antiviral effect, however, hemagglutination activity was shown in all of 6 test samples at 50 μg/ml and 100 μg/ml, suggesting that virus proliferation was not inhibited.

On the other hand, in the sample added with the 95% ethanol extract (at 80° C.), hemagglutination did not occur in all of 6 test samples at 400 μg/ml and 200 μg/ml showing that virus proliferation was completely inhibited, hemagglutination occurred in two of 6 test samples at 100 μg/ml, showing partial antiviral effect, and hemagglutination occurred in five of 6 test samples at 50 μg/ml, showing weak antiviral effect. The sample added with 95% ethanol extract (at 60° C.) showed the same hemagglutination results as those of the 95% ethanol extract (at 80° C.). The 95% ethanol extract (at 40° C.) showed the same hemagglutination as those of the 95% ethanol extracts (at 80° C., 65° C., respectively) at 400 μg/ml and 200 μg/ml, and thus, no hemagglutination activity was shown in all samples, suggesting that viral proliferation was completely inhibited, and showed partial antiviral effect hemagglutination occurred in one of 6 test samples at 100 μg/ml and three of 6 test samples at 50 μg/ml, thus confirming that the extract shows high antiviral at various effect even at low concentration.

Based on extract concentration of 100 μg/ml, antiviral activity at various solvents was in the order: 95% ethanol extract (at 40° C.)>95% ethanol extract (at 80° C.) and 95% ethanol extract (at 60° C.)>water extract (at 100° C.). Therefore, it was determined that 95% *Alnus japonica* extract (at 40° C.) is most suitable as the *Alnus japonica* extract to prepare the inventive antiviral composition.

In order to compare antiviral effects according to *Alnus japonica* with different origins, extracted at 40° C. at which the highest inhibition effect on virus proliferation was shown and various extract solvents, the same experiment as described above was performed under conditions shown in Table 2.

TABLE 2

| Control | | Raw materials to be extracted and solvents | Alnus japonica extracts (μg/ml) | | | |
|---|---|---|---|---|---|---|
| non-virus | virus | | 100 | 50 | 25 | 12.5 |
| 6/6 | 0/6 | the bark of Korean native Alnus japonica 80% ethanol extract | 2/6 | 4/6 | 6/6 | 6/6 |
| | | the bark of Korean native Alnus japonica 95% ethanol extract | 1/6 | 3/6 | 4/6 | 5/6 |
| | | the stem of Korean native Alnus japonica 80% ethanol extract | 3/6 | 5/6 | 6/6 | 6/6 |
| | | the stem of Korean native Alnus japonica 95% ethanol extract | 1/6 | 3/6 | 6/6 | 6/6 |
| | | the bark of Chinese native Alnus japonica 80% ethanol extract | 1/6 | 4/6 | 6/6 | 6/6 |
| | | the bark of Chinese native Alnus japonica 95% ethanol extract | 1/6 | 5/6 | 6/6 | 6/6 |

As a result, as shown in Table 2, it was observed that 80% and 95% ethanol extracts of the bark of Korean indigenous *Alnus japonica* showed excellent antiviral activity, compared to 80% and 95% ethanol extracts of the stem of Korean indigenous *Alnus japonica*. Thus, it could be confirmed that the bark was suitable for use as *Alnus japonica* extract for the inventive antiviral composition.

When comparing *Alnus japonica* from different origins, 80% ethanol extracts of the bark of Korean indigenous *Alnus japonica* and Chinese indigenous *Alnus japonica* showed similar activity, and 95% ethanol extract of the bark of Korean native *Alnus japonica* showed more excellent activity than that of 95% ethanol extract of Chinese native *Alnus japonica*, and when comparing antiviral activities at various extract solvents, 95% ethanol extract showed higher antiviral activities than that of 80% ethanol extract.

From the above the results, it could be confirmed that 95% ethanol extract of the bark of Korean native *Alnus japonica* extracted at 40° C. shows the most excellent antiviral effect.

Hereinafter, examples of preparations of the pharmaceutical composition comprising an *Alnus japonica* extract according to the present invention, however, these examples are for illustrative purpose only and are not construed to limit the scope of the present invention.

Preparation Example 1

Powder Preparation

Extract of *Alnus japonica*: 20 mg
Lactose: 100 mg
Talc: 10 mg

The above ingredients were mixed, and changed in an air-tight pack to prepare a powder preparation Preparation Example 2

Tablet Preparation

Extract of *Alnus japonica*: 10 mg
Cornstarch: 100 mg
Lactose: 100 mg
Stearin magnesium: 2 mg The above ingredients were mixed, and tableted according to the conventional method to prepare tablets.

Preparation Example 3

Capsule Preparation

Extract of *Alnus japonica*: 20 mg
Crystalline cellulose: 13.3 mg
Lactose: 65.8 mg
Magnesium stearate: 0.9 mg The above ingredients were mixed, and changed in a gelatin capsule according to the conventional method to prepare capsules.

Preparation Example 4

Injection Preparation

Extract of *Alnus japonica*: 10 mg
Mannitol: 180 mg
Sterile distilled water for injection: 2,974 mg
$Na_2HPO_4 \cdot 12H_2O$: 26 mg The above ingredients were added to an ample at the amount shown above per ampule (3 ml) according to the conventional preparation method of injectable solution.

Preparation Example 5

Liquid Preparation

Extract of *Alnus japonica*: 20 mg
Isomerized sugar: 10 g
Mannitol: 5 g
Proper quantity of purified water Each ingredient was dissolved in the purified water and added with a suitable amount of lemon flavor to mix the above ingredients, then the purified water was added to a total volume of 100 ml, followed by sterilizing to change in a brown vial, thus preparing liquid preparation, according to the conventional liquid preparation method.

INDUSTRIAL APPLICABILITY

As described above in detail, the extract of the bark or stem of *Alnus japonica* according to the present invention has low toxicity to choriollantonic cells which is a normal cell, while having an excellent antiviral effect even when administered at low concentration. Therefore, the composition comprising the *Alnus japonica* extract can be used effectively in preventing and treating influenza viral infection.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof. It is understood that numerous changes and modifications can be made by those skilled in art without departing from the invention concepts disclosed herein.

What is claimed is:
1. A method of treating an avian influenza viral infection in a subject in need thereof, the method comprising administering an effective amount of a composition comprising an extract of the bark of *Alnus japonica* to the subject to treat the avian influenza viral infection, wherein said extract of the bark of *Alnus japonica* is prepared by a method comprising the steps of:
- (a) extracting the bark of Korean indigenous *Alnus japonica* with 80~100% alcohol at 30~80° C.; and
- (b) recovering the resulting extraction solution at the same temperature by vacuum concentrating and drying.

2. The method of claim 1, wherein said alcohol is ethanol.

3. The method of claim 1, wherein the effective amount is between about 0.01 and about 200 mg/kg subject per day.

4. The method of claim 1, wherein the effective amount is between about 0.1 and about 100 mg/kg subject per day.

5. The method of claim 1, wherein the composition is administered to the subject as a tablet.

6. The method of claim 1, wherein the avian influenza virus is KBNP-0028 (KCTC 10866BP).

\* \* \* \* \*